United States Patent [19]
Hasson

[11] Patent Number: 5,338,302
[45] Date of Patent: Aug. 16, 1994

[54] VAGINAL STABILIZER CANNULA

[76] Inventor: Harrith M. Hasson, 2551 N. Clark, 8th Floor, Chicago, Ill. 60614

[21] Appl. No.: 56,713

[22] Filed: May 3, 1993

[51] Int. Cl.⁵ .................. A61M 25/01; A61M 25/10
[52] U.S. Cl. ................................. 604/105; 604/101
[58] Field of Search ............... 604/101, 106, 174, 175, 604/179

[56] References Cited

U.S. PATENT DOCUMENTS

| | | | |
|---|---|---|---|
| 507,573 | 10/1893 | Wetherbee | 604/105 |
| 1,870,942 | 8/1932 | Beatty | 604/105 |
| 2,693,191 | 11/1954 | Raiche | 604/101 |
| 2,849,001 | 8/1958 | Oddo | 604/101 |
| 3,108,595 | 10/1963 | Overment | 604/105 |
| 3,241,554 | 3/1966 | Coanda | 604/105 |
| 3,788,328 | 1/1974 | Alley et al. | 604/178 |
| 3,915,171 | 10/1975 | Shermeta | 604/101 |
| 4,069,826 | 1/1978 | Sessions et al. | 604/178 |
| 4,089,337 | 5/1978 | Kronner | 604/178 |
| 4,423,725 | 1/1984 | Baran et al. | 604/101 |
| 4,666,433 | 5/1987 | Parks | 604/178 |
| 4,798,592 | 1/1989 | Parks | 604/178 |
| 5,092,850 | 3/1992 | Buma | 604/178 |
| 5,163,906 | 11/1992 | Ahmadi | 604/101 |

*Primary Examiner*—Paul J. Hirsch
*Attorney, Agent, or Firm*—Wood, Phillips, VanSanten, Hoffman & Ertel

[57] ABSTRACT

A cannula having a sleeve with a body having proximal and distal ends and defining a through passageway. First structure is provided on the body to define a first shoulder to abut a tissue wall through which the body extends. Second structure is provided on the body to define a second shoulder to abut a tissue wall through which the body extends. The first and second structures are spaced from each other to permit the first and second shoulders to abut separate, spaced tissue walls through which the body extends.

24 Claims, 1 Drawing Sheet

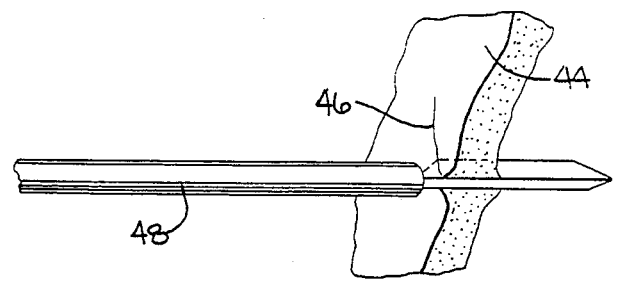
FIG. 1
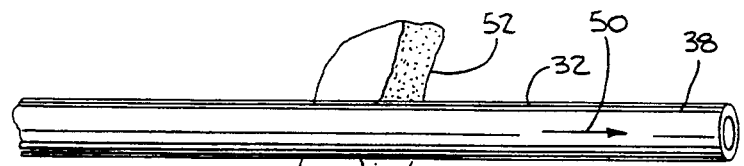
FIG. 2
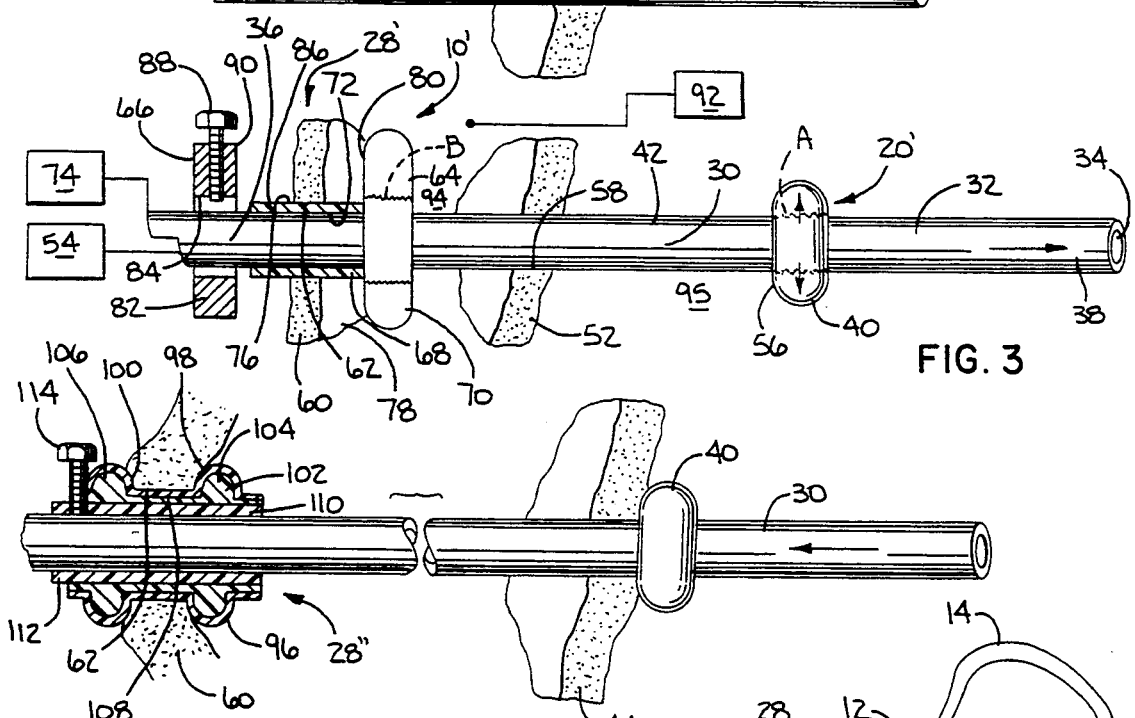
FIG. 3
FIG. 4
FIG. 6
FIG. 5

VAGINAL STABILIZER CANNULA

BACKGROUND OF THE INVENTION

1. Field of the Invention

This invention relates to medical instruments, such as those used in laparoscopy, and, more particularly, to a cannula with spaced sealing and stabilizing structures.

2. Background Art

Many surgical procedures are performed through an incision in the abdominal area of a patient. In laparoscopy, such an incision is normally small, however, a scar nonetheless remains.

Certain regions accessed through the abdomen could be accessed from internally through the wall of the vagina with entry gained thereto through the vaginal canal, especially for removal of tissues excised by laparoscopic technique. However, heretofore, this type of procedure has not been practical in that it has not been possible to controllably introduce an instrument, stabilize that instrument, and afford the space to allow the required manipulation of the instrument. While a cannula, such as that shown in my U.S. Pat. No. 5,002,557, can be used to stably support an instrument on the vaginal wall, once the membrane on the cannula therethrough is deflated during vaginal removal of tissues, the pneumoperitoneum gas escapes due to loss of the single sealing member, This makes further manipulation of the cannula virtually impossible. It may be difficult or impossible to orient the cannula as precisely as required to access the area at which a further procedure is to be performed.

SUMMARY OF THE INVENTION

The present invention is specifically directed to overcoming the above-enumerated problems in a novel and simple manner.

The invention is directed to a cannula having a sleeve with a body having proximal and distal ends and defining a through passageway. First structure is provided on the body to define a first shoulder to abut a tissue wall through which the body extends. Second structure is provided on the body to define a second shoulder to abut a tissue wall through which the body extends. The first and second structures are spaced from each other to permit the first and second shoulders to abut separate, spaced tissue walls through which the body extends.

While the inventive cannula has a number of different practical applications, it is highly useful in accessing a region in which surgery is to be performed through the vaginal canal and an opening defined by an incision in the vagina at the apex.

In one form, the shoulders seal around either a natural opening or an opening made by an incision. Each shoulder can be defined by a deformable membrane that is selectively inflated and deflated. By deflating the membrane to a collapsed state, it is extendable through a tissue opening without significant interference. It can thereafter be inflated to define the sealing shoulder.

In one form, the spacing between the first and second structures, and the shoulders defined thereby, can be varied. Both of the first and second structures may be movable between the ends of the body. Alternatively, one of the structures can be fixed relative to the sleeve while the other one is movable.

The movable structure may have a guide sleeve that is slidable along the body between the ends thereof. Structure can be provided to fix the guide sleeve in a desired location relative to the body.

In one form, one of the first and second structures has first and third shoulders to captively engage a tissue wall through which the sleeve extends. The first and second shoulders can be defined by a single, resilient membrane. The membrane can be hollow or surround a compressible material, such as foam. The membrane and/or the foam may be made with a generally cylindrical shape with there being a reduced diameter portion between the first and second shoulders. The wall of the tissue, through which the body extends, nests in the reduced diameter portion, with the bounding shoulders effecting a positive seal and also stabilizing the cannula within the tissue.

With the above structure, the distended abdominal cavity can be accessed through the vagina without loss of the pneumoperitoneum gas. The cannula can be extended through spaced walls and supported sealingly thereon. This sealed arrangement, in addition to stably mounting the cannula, allows the distention of the vagina with the pneumoperitoneum gas without loss thereof by reason of the provision of a second sealing member which seals the vagina from the outside. This arrangement facilitates the performance of a wide range of surgical procedures.

The invention further comprehends a cannula having a sleeve with first and second sealing structures with the first sealing structure being positionable selectively in a) a first state wherein it does not project significantly from the peripheral surface of the body to allow the first sealing structure to be extended into and withdrawn from a tissue opening without interference and b) a second state wherein the first sealing structure defines a shoulder to abut a wall on tissue surrounding an opening through which the body extends, and second sealing structure defining a second shoulder to abut a tissue wall around an opening through which the body extends. The first and second shoulders are repositionable along the body to allow openings in first and second separate, spaced tissue walls to be sealed by the first and second shoulders.

In one form, one of the first and second sealing structures includes a clamp for captively maintaining a tissue between the clamp and one of the first and second shoulders.

One of the first and second sealing structures may have a guide sleeve that is movable along the body between the ends of the body. The clamp can be placed in a locked state in which it bears the guide sleeve against the body to prevent relative movement therebetween. The clamp defines a shoulder which cooperates with the shoulder on the one of the first and second sealing structures to positively embrace a tissue and seal the opening through which the body extends.

The invention further contemplates a method of defining a working passageway through openings in first and second spaced tissue walls, with the method including the steps of: providing a sleeve having proximal and distal ends, with the sleeve having a body defining a through passageway and having a peripheral surface with first and second shoulder defining structures thereon; placing the first shoulder defining structure in a first state so that it does not project significantly beyond the peripheral surface of the sleeve body; directing the distal end of the body and the first shoulder defining structure consecutively through first and second tissue openings so that the first shoulder defining structure projects through the second tissue opening; placing the first shoulder defining structure in a second state so that a first shoulder is defined that is abuttable to the second tissue to prevent withdrawal of the first shoulder defining structure from the second tissue opening; drawing the first shoulder against the second tissue; and connecting the second shoulder defining structure to the first tissue to stabilize the sleeve relative to the first and second tissues.

In one form, the second shoulder defining structure is caused to seal the opening in the first tissue.

BRIEF DESCRIPTION OF THE DRAWINGS

FIG. 1 is an elevation view of a portion of a tissue with a scalpel being used to define an incision therethrough;

FIG. 2 is an elevation view of a portion of a cannula, according to the present invention, extending through an opening defined by the incision in a tissue wall;

FIG. 3 is an elevation view of one form of the inventive cannula in the process of being operatively connected through spaced tissue walls;

FIG. 4 is a modified form of cannula, according to the present invention, shown in an operative position on spaced tissue walls;

FIG. 5 is a still further modified form of cannula, according to the present invention, operatively connected through spaced tissue walls; and FIG. 6 is a schematic representation of the inventive cannula operatively connected through a vagina.

DETAILED DESCRIPTION OF THE DRAWINGS

In FIG. 6, one environment is shown for use of the inventive cannula, which is shown schematically at 10 in FIG. 6 and in detail in FIGS. 1-5. In FIG. 6, a vagina 12 and uterus 14 are shown in schematic form. This is but one suitable environment for use of the present invention and should not be viewed as limiting.

The cannula 10 is directed through the vaginal opening/canal 16 and through the wall 18 of the vagina 12 at a location remote from the opening 16. First sealing means 20 supports the distal end 24 of the cannula on the wall 18 of the vagina 12 and seals around the opening 26 defined by an incision through the wall 18. The proximal end 27 of the cannula 10 is stabilized by a second sealing means 28 which also seals around the vaginal opening/canal 16 defined in the wall portion 30.

With the inventive structure, it is possible to direct a cannula through spaced tissues and to use both tissues as a support for the cannula 10. Extension of the cannula 10 through the spaced walls stabilizes the cannula 10 and rigidifies, in this case, the vagina.

One form of the cannula 10' will be described with respect to FIGS. 1-3. The cannula 10' has an elongate, cylindrical sleeve 30 with a body 32 defining a through passageway 34 between proximal and distal ends 36, 38, respectively, thereof.

A first sealing means 20' includes an inflatable membrane 40 which can be placed selectively in a collapsed state, as shown in phantom lines at A in FIG. 3, and an expanded state, as shown in solid lines. The membrane 40 is at a fixed location on the body 32 and, in the collapsed state, the membrane 40 does not project significantly beyond the peripheral surface 42 of the body 32. This allows the membrane 40 to be directed fully through a tissue opening without interfering with the tissue wall.

In FIG. 1, an exemplary tissue wall 44 is shown. An incision 46 is made through the wall using a scalpel 48. The incision 46 can be made just slightly larger than the diameter of the sleeve body 32. The distal end 38 of the body 32 can be advanced in the direction of the arrow 50 through the incision 46, with the membrane 40 collapsed, until the membrane 40 is fully exposed beyond the surface 52 of the tissue wall 44.

Through a means, shown schematically at 54, the membrane 40 can be selectively inflated and deflated. A suitable structure to accomplish this is described in detail in my U.S. Pat. No. 5,002,557. Once the membrane 40 is inflated, an annular shoulder 56 is defined by the membrane 40. The shoulder 56 can be drawn against the tissue surface 52 to thereby seal around the opening 58 defined by the incision 46. The shoulder 56 prevents withdrawal of the sleeve 30 so long as the membrane 40 is inflated.

A second sealing means 28' can then be connected to a separate tissue wall 60 spaced from the tissue wall 44. The tissue wall 60 has an opening 62 therethrough that may be a natural opening, as in the case of the vaginal opening/canal 16, or an opening defined by an incision, such as the incision 46.

The second sealing means 28' includes cooperating first and second parts 64, 66. The first part 64 consists of a guide sleeve 68 with an inflatable membrane 70 thereon. The guide sleeve 68 has an inside surface 72 that closely surrounds the peripheral surface 42 of the sleeve 30 and is movable thereagainst lengthwise between the proximal and distal ends 36, 38.

The membrane 70 is selectively inflated and deflated through a means 74, which may be the same, or a like functioning structure, as the means 54. By deflating the membrane 70 to the state shown in phantom lines at B, the membrane 70 does not project radially significantly beyond the outer surface 76 of the guide sleeve 68. Consequently, the membrane 70 and guide sleeve 68 can be directed through the tissue opening 62 without significant interference. Once the membrane 70 is directed fully through the tissue walls 60 to be exposed beyond the wall surface 78, the membrane 70 can be inflated through the means 74 to define an annular shoulder 80 to abut to the surface 78. This effects a seal around the opening 62 in the same manner as the membrane 40 seals the opening 58.

The second part 66 of the second sealing means 28' is a clamp. The clamp 66 consists of an annular ring 82 with a through bore defined by a surface 84 having a diameter slightly larger than the diameter of the outer surface 76 of the guide sleeve 68. The clamp 66 then be placed over the exposed, external portion 86 of the guide sleeve 68.

A set screw 88 is directed radially through the clamp 66, and upon being tightened against the guide sleeve 68, fixes the clamp 66 relative to the guide sleeve 68 and, in so doing, presses the guide sleeve 68 against the peripheral surface 42 of the body 32 to lock the guide sleeve 68 in a desired position on the sleeve 30.

The clamp 66 has an annular shoulder 90 which, in conjunction with the shoulder 80 on the membrane 70, captively embraces the tissue wall 60.

Gas from a supply 92 can be introduced to the space 94 that is bounded by the tissue walls 44, 60. In the case of a vagina, gas will be introduced into the abdominal cavity 95 which, in the absence of the sealing means 20', is in free communication with the vagina through the incision 46. When the sealing membrane 40 is deflated, the sealing member 70 confines the gas within the space 94, maintaining the pneumoperitoneum and allowing surgery to proceed, as in the abdominal cavity.

The cannula 10' is thus stably supported in an operative position relative to the tissues 44, 60. Surgical procedures can be performed through the sleeve 30 without forming an external incision. The spaced support of the cannula 10' rigidifies the tissue walls 44, 60 so that instruments can be consistently directed into and withdrawn from the passageway 34 as need dictates.

The invention further contemplates the method of placing the cannula 10' in its operative position. To accomplish this, both membranes 40, 70 are collapsed. The sleeve 30 is directed through the first tissue 52 to expose the membrane 40, which is then inflated. The sleeve 30 is drawn outwardly to sealingly place the shoulder 56 against the tissue wall 52. The guide sleeve 68 is then pressed through the tissue wall 60 until the membrane 70 is fully exposed to allow its inflation. Once inflated, the exposed portion 86 of the guide sleeve 68 is pulled outwardly to seat the shoulder 80 sealingly against the tissue wall 60. The clamp 66 is then placed over the guide sleeve 68, pushed firmly against the wall 60 and the set screw 88 turned to effect locking of the clamp 66 relative to the guide sleeve 68 and in turn locking of the guide sleeve 68 relative to the sleeve body 32. The guide sleeve 68 is preferably made from material that is resilient enough to allow its deformation under the force of the threaded set screw 88.

A slightly modified form of second sealing means is shown at 28" in FIG. 4. The sealing means 28", rather than having a two part construction, has a single membrane 96 that defines facing shoulders 98, 100 which captively bound the tissue 60, which is shown to be the tissue surrounding the vaginal opening/canal 16.

The membrane 96 conforms to a cylindrical body 102, which is resilient to allow it to be readily deformed. The body 102 may be made from foam rubber, or the like. The body 102 has enlarged, axially spaced portions 104, 106 defining the shoulders 98, 100, respectively, with there being a reduced diameter portion 108 therebetween for seating the tissue wall 60.

The body 102 and surrounding membrane 96 are built over a guide sleeve 110, which is movable along the body 30. The guide sleeve 110 has an exposed portion 112 through which a set screw 114 is threadably directed.

With the membrane 40 seated against the tissue wall 44, as previously described, the second sealing means 28" can be pressed through the opening 62 into the operative position shown in FIG. 4. The body 102 is sufficiently resilient to allow this to occur and has sufficient memory that it reassumes the undeformed state shown in FIG. 4. The membrane 96 serves primarily a sealing function to prevent penetration of the foam body 102 by any moisture.

A further modified form of the second sealing means is shown at 28''' in FIG. 5. The sealing means 28''' includes a membrane 116 that may be made of rubber or other suitable material. The membrane 116 has the same peripheral shape as the body 102, to define facing shoulders 118, 120 and a reduced diameter portion 122 to seat the wall 60. The membrane 116 can be selectively inflated and deflated through a means 124. By deflating the membrane 116, it can be readily collapsed and directed through the tissue opening 62, whereupon it can be inflated to effect a positive seal at the opening 62. Inflation of the membrane 116 can be effected to the extent necessary to maintain a seal. More positive sealing can be achieved than with the preformed body 102 in FIG. 4 by increasing the pressure within the membrane 116.

The foregoing disclosure of specific embodiments is intended to be illustrative of the broad concepts comprehended by the invention.

I claim:

1. A cannula comprising:

a sleeve having a body with proximal and distal ends and defining a through passageway communicating between the proximal and distal body ends.

said proximal and distal body ends being open to allow a surgical instrument to be directed into the proximal body end through the body passageway and out the distal body end;

first means on the body defining a first shoulder facing in a first direction to abut a tissue wall through which the body extends; and second means on the body defining a second shoulder facing in the first direction to abut a tissue wall through which the body extends, said first and second means being spaced from each other to permit said first and second shoulders to abut spaced tissue walls through which the body extends.

2. The cannula according to claim 1 wherein the first and second shoulders each have surfaces facing lengthwise of the body for sealing fully around an opening in a tissue wall through which the body extends.

3. The cannula according to claim 1 wherein at least one of the first and second shoulders is defined by a material that is sufficiently deformable to sealing conform to a tissue against which is pressed.

4. The cannula according to claim 1 wherein one of the first and second means is at a fixed location on the sleeve.

5. The cannula according to claim 1 wherein one of the first and second means is selectively movable between the ends of the body to allow the spacing between the first and second shoulders to be altered.

6. The cannula according to claim 1 wherein at least one of the first and second means includes an inflatable membrane defining one of the first and second shoulders.

7. The cannula according to claim 1 wherein the first means includes oppositely facing first and third shoulders to captively engage a wall of tissue through which the body extends at a location spaced from the second shoulder.

8. The cannula according to claim 7 wherein the first and third shoulders are defined by a single, resilient membrane.

9. The cannula according to claim 8 wherein the membrane surrounds a compressible material, said compressible material having a generally cylindrical configuration with said first and third shoulders being axially spaced from each other and there being a reduced diameter portion between the first and third shoulders.

10. The cannula according to claim 7 wherein the first means includes a guide sleeve, there being means cooperating between the guide sleeve and body for guiding movement of the first means between the proximal and distal ends of the body over a predetermined range.

11. The cannula according to claim 10 including means for fixing the position of the first means relative to the body.

12. The cannula according to claim 1 wherein at least one of the first and second means includes an inflatable membrane that can be selectively placed in a) a collapsed state and b) inflated state.

13. The cannula according to claim 12 including means for selectively placing the inflatable membrane in collapsed and inflated states.

14. A cannula comprising:
   a sleeve having a body with a peripheral surface, proximal and distal ends, and defining a through passageway through which access can be gained to a cavity into which the body extends;
   first means on the body for sealing around an incision in a first tissue wall,
   said first means being positionable selectively in a) a first state wherein the first means does not project significantly from the peripheral surface of the body to allow the first means to be extended into and withdrawn from an opening without significant interference and b) a second state wherein the first means defines a first shoulder to abut a wall of tissue surrounding an opening through which the body extends;
   second means on the body for defining a second shoulder to abut a tissue wall around an opening through which the body extends;
   said second means including means for captively holding a tissue wall in conjunction with the second shoulder at a location spaced from the first sealing means; and
   means for altering the relative positions of the first and second shoulders to allow openings in first and second spaced tissue walls to be sealed by the first and second shoulders.

15. The cannula according to claim 14 wherein there are means cooperating between at least one of the first and second means and body for allowing the position of the shoulder on the one of the first and second means to be altered relative to the shoulder on the other of the first and second means.

16. The cannula according to claim 14 wherein at least one of the first and second means includes an inflatable membrane defining one of the first and second shoulders.

17. The cannula according to claim 14 wherein the means for captively holding a tissue wall in conjunction with the second shoulder includes a clamp for captively maintaining a tissue between the clamp and second shoulder.

18. The cannula according to claim 17 wherein the second means includes a guide sleeve that is movable along the body between the ends of the body, the second shoulder being carried by the guide sleeve, the clamp defines a shoulder and means cooperate between the clamp and guide sleeve to fix the relative positions of the clamp shoulder and second shoulder.

19. The cannula according to claim 18 wherein the means cooperating between the clamp and guide sleeve in a locked state urges the guide sleeve against the body to prevent relative movement therebetween.

20. A method of defining a working passageway through openings in first and second spaced tissue walls, said method comprising the steps of:
   providing a sleeve with a body defining a through passageway and having a peripheral surface, first and second shoulder defining means, and open proximal and distal ends;
   placing the first means in a first state so that the first means does not project significantly beyond the peripheral surface of the sleeve body;
   directing the distal end of the body and the first means consecutively through first and second tissue openings so that the first means projects through the second tissue opening;
   placing the first means in a second state so that a first shoulder is defined that abuts the second tissue to prevent withdrawal of the first means from the second tissue opening;
   drawing the first shoulder against the second tissue; and
   connecting the second means to the first tissue at a location spaced from the second tissue wall to stabilize the sleeve relative to the first and second tissue walls.

21. The method according to claim 20 including the step of causing the second means to seal the opening in the first tissue.

22. The method according to claim 20 wherein the first and second tissues bound a vaginal cavity and the step of directing the distal end of the body comprises the step of directing the distal end of the body through the vaginal canal.

23. The method according to claim 20 including the step of moving the second means between the ends of the body to abut the second means to the first tissue wall.

24. The method according to claim 23 including the step of providing a third shoulder on the body and captively holding the second tissue wall between the first and third shoulders.

* * * * *